United States Patent [19]

Turner et al.

[11] Patent Number: 4,856,515
[45] Date of Patent: Aug. 15, 1989

[54] AUTOMATIC LANCET

[76] Inventors: Robert C. Turner, 13 Belbroughton Road, Oxford OX2 6UZ; Rury R. Holman, Shrublands, Faringdon Road, Cumnor, Oxford, OX2 9QY, both of England

[21] Appl. No.: 63,874
[22] Filed: Jun. 19, 1987
[30] Foreign Application Priority Data Jun. 19, 1986 [GB] United Kingdom ............... 8614970

[51] Int. Cl.⁴ .............................................. A61B 17/34
[52] U.S. Cl. .................................. 128/315; 128/329 R
[58] Field of Search ............... 128/314, 315, 329 R, 128/751, 753, 754; 604/46; 30/128, 368

[56] References Cited

U.S. PATENT DOCUMENTS

| | | | |
|---|---|---|---|
| 2,126,640 | 8/1938 | Johnson | 30/368 |
| 2,496,111 | 1/1950 | Turkel | 128/754 |
| 4,230,118 | 10/1980 | Holman et al. | 128/314 |
| 4,658,821 | 4/1987 | Chiodo et al. | 128/314 |

FOREIGN PATENT DOCUMENTS 1161719 2/1984 Canada ................... 128/314

Primary Examiner—Dalton L. Truluck
Assistant Examiner—Denise Whelton
Attorney, Agent, or Firm—Millen, White & Zelano

[57] ABSTRACT

An automatic lancet device comprising a housing with a recess in one side through which a mounting member can move to carry a lancet from a retracted to an operative position, and a finger guard through which or past which the lancet makes its finger piercing movement in use. The finger guard is provided with a stem dimensioned to be removably located in a recess in the housing. A displacement member is permanently mounted on the device and is movable from a first position to a second position to cause displacement of the finger guard from the recess, the displacement being achievable by actuation at a location remote from the finger guard.

1 Claim, 2 Drawing Sheets

AUTOMATIC LANCET

BACKGROUND OF THE INVENTION

The present invention relates to a lancet device for performing a pricking operation, for example for use in taking skin capillary blood samples.

Our granted British Patent No. 1599654 describes and claims one particular form of automatic lancet device, which is characterized by the lancet travelling a curved path for example being carried by an arm which rotates around a pivot. The present invention is applicable to devices including devices of that type.

The present invention is concerned with lancet devices in which a finger guard (referred to in G.B. No. 1599654 as a disposable foot) is provided against which the finger rest in use, and through which or past which the lancet makes the pricking action. The guard prevents the lancet from penetrating the finger too far and reassures the user as well as assisting in locating the lancet device on the finger for use.

Whilst ejection of the used lancet without the need to contact it with one's fingers is provided for in the known device no such provision has yet been proposed or made in respect of the finger guard. The finger guard is also liable to become contaminated with blood after it has been used and despite the increasing concern about the risk of infection from contaminated blood of other users and medical personnel e.g. in hospitals, some years have passed before we came to the conclusion that this risk could be diminished by providing for mechanical ejection of a finger guard from the lancet device by operation of an ejector at a location removed from the finger guard.

SUMMARY OF THE INVENTION

According to the present invention the finger guard is mounted on the device so as to be displaceable therefrom. Preferably displacement means are permanently mounted on the device and are movable from a first position to a second position so that the said movement causes displacement of the finger guard from the device, the said movement being achievable actuation at a location remote from the finger guard.

Preferably the displacement means are such as to directly engage the finger guard and displace it fully from its recess in the lancet device. The device can thus be aimed at a receptacle and the displacement means operated to in effect project the finger guard into the receptacle, such projection being readily aided by gravity.

Indirect displacement of the finger guard is not excluded.

In a preferred embodiment, the lancet device is automatic in the sense that the lancet itself is biassed to pierce the finger and is then latched and actuation merely involves the user releasing the latch so that the biassing then drives the lancet into the user's finger. This biassing is normally achieved by a mechanical spring but any effective mechanism could be used.

The finger guard may be a plate with a hole or notch in it through which the lancet travels and a stem. The stem is desirably a push fit or a more or less tight fit in a slot or hole in the body of the lancet device. A balance must be struck between the desire for a fit tight enough to prevent accidental falling out of the finger guard and loose enough to permit ready ejection with needing too powerful a mechanism or too much effort by the user. The arrangement should desirably also be such that jamming of the stem in the recess is avoided.

The term stem is to be understood broadly as anything apt to achieve the necessary function of holding the finger guard portion ready for the piercing operation and in secured and known relationship to the lancet's site of action whilst also being such as to transmit the ejecting force of the displacement means.

It may be a plate or rod which may be solid or pierced and of any appropriate cross-section. It is desirably stiff but could tolerate a degree of flexibility so long as this did not interfere with its function.

The finger guard is preferably made of moulded plastics material and is stiff. The finger guard may be positively located as by some latch or functional engagement between it and its mounting or the stem may merely be of such a length that the finger guard tends to stay in the mounting due to the stem engaging, e.g. frictionally, the walls of the hole or recess.

The displacement means preferably have an actuating member which on movement of the displacement means from the first to the second position displaces the finger guard e.g. by engaging the stem of the finger guard. The displacement means may also have a remote activating surface extending out through a surface of the device remote from the finger guard so that a finger can be used to move the displacement means from the first to the second position without the finger coming into contact with the finger guard.

If desired the displacement means could be in two or more parts. Also the displacement means could be biassed and latched so that engagement of the activating surface would cause the finger guard to be projected away from the device e.g. facilitating its direction into a disposal bin. The insertion of a new finger guard could be arranged in effect to cock such biassable displacement means by loading the biassing mechanism and engaging a latching mechanism. The biassing mechanism could conveniently be a spring e.g. a mechanical spring such as a compression spring or a torsion spring.

One convenient and preferred form of displacement means is a captive bolt located in a slot, hole or recess in the body of the device which communicates with the recess in which the finger guard is mounted.

The bolt will desirably also have an activating surface engagable from outside the device at a location remote from the finger guard, or engagable or activatable by a further member which itself is engagable from outside the device.

Another form of displacement means may be a lever or levers pivoted to the device and actuatable from outside the device at a location remote from the finger guard so as to move a part of the lever or levers or one of the levers from a first to a second position whereby the finger guard is displaced. The pivot may be between the activating surface and the point of engagement with the finger guard or may be beyond the point of engagement with the finger guard.

The lancet device may be provided with latching mechanisms to prevent accidental displacement of the finger guard, and such latching mechanisms could engage either the finger guard or the displacement means, e.g. the captive bolt or lever of the above two specific forms of the invention. The device may also be provided with biassing and latching mechanisms as discussed above.

The invention may be carried into practice in various ways, but one specific embodiment thereof will now be described by way of example only with reference to a lancet device of the type shown in G.B. No. 1599654 and with reference to the accompanying drawings, in which:

DESCRIPTION OF THE PREFERRED EMBODIMENT

Figure 1:
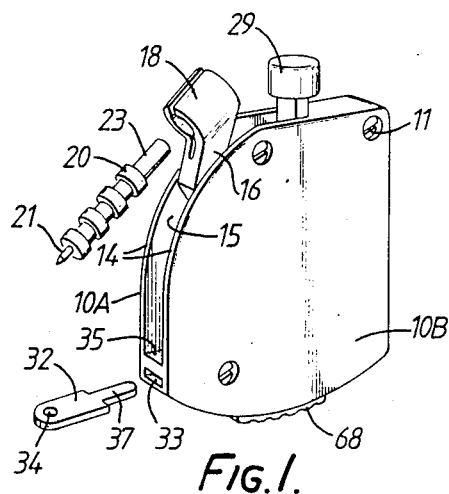
FIG. 1 is a perspective view of a lancet device with a needle and a finger guard in position for fitting.

The device comprises a two-part, preferably plastic, housing of generally quadrant shape having a base 10A and a separate detachable cover 10B, which can be mutually located by means of co-operating interengageable formations (not shown) and held together by screws 11. The two housing portions 10A and 10B have arcuate edges 14 between which a slot 15 is defined, and an arm 16 is pivotally mounted at its inner end in the housing by means of a pivot pin 17, and protrudes at its outer end through the slot 15. The axis of the pivot pin 17 is concentric with the edges.

At its outer end the arm has a holder 18 in the form of a cylinder with a bore opening through its lower end, which can receive and hold the ribbed mounting 20 of a mounted needle 21, to hold the needle with its pointed tip projecting generally tangentially with respect to the edges 14 and the pivot pin 17. The needle 21 has a protuberance 23 at its end remote from the tip by which a used needle can be pushed down or pulled up out of the bore in the holder 18. The bore may be slotted so as to give a spring engagement to the mounting of the needle.

Figure 4:
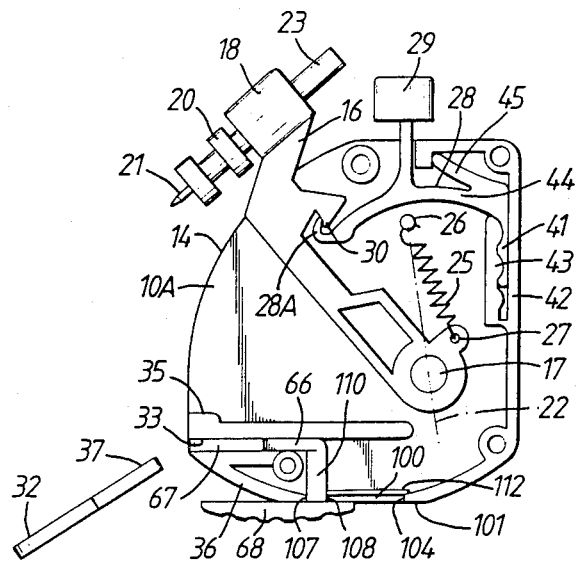
FIG. 4 is an elevation of the device with the cover removed and in the cocked position.

A helical tension spring 25 extends between an anchorage pin 26 on the base 10A and an eye 27 formed on the arm 16 near its pivoted end, the eye 27 being radially-offset from the pivot pin 17. In a position of the arm intermediate between those shown in FIGS. 5 and 4 the spring 25 is directly aligned with the pivot pin 17 along the axis 22 so that it exerts no turning torque on the arm 16. That position of the arm 16 is thus a neutral or dead-centre position. When the arm is rotated in the clockwise direction in FIGS. 4 and 5 to a cocked position at the top end of the slot 15, the spring 25 will be extended and will exert a resilient torque on the arm 16 tending to turn the arm towards its neutral position; a resilient latch member 28 with a latch hook 28A and an operating trigger 29 is mounted in the base 10A to co-operate with a hook 30 formed in the arm 16 to latch the arm in its cocked position as shown in FIG. 4.

The latch member 28 is a plastic moulding with a stem 41 which is keyed into a slot defined between the rear wall 42 of the base and a projection 43 moulded integrally with the base. From the stem 41 an arcuate cantilever arm 44 extends towards the front of the device carrying the hook 28A at its end. The trigger 29 projects up through a slot in the top of the base 10A for manual operation. An integrally moulded spring tongue 45 acts against the edge of the base to bias the cantilever arm 44 in a direction to hold the hook engaged. Pressure on the trigger 29 will release the latch by disengaging the hooks 28A and 30 to allow the spring 25 to rotate the arm in the anti-clockwise direction in FIGS. 4 and 5 back to its neutral position. The inertia of the swinging arm will carry it through its neutral position for a pricking operation as will now be described.

Figure 5:
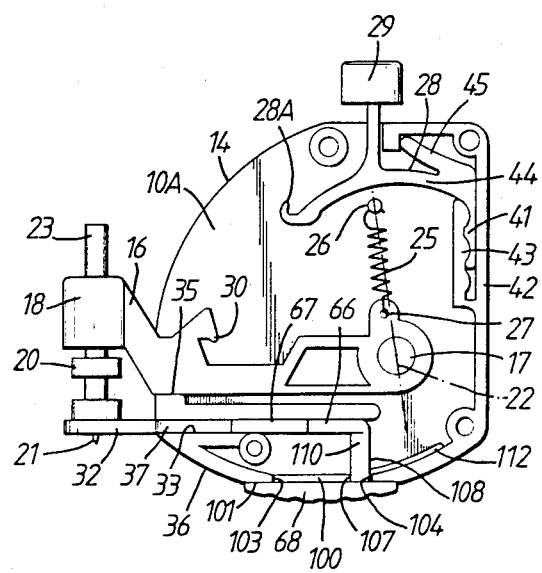
FIG. 5 is a view corresponding to FIG. 4 with the needle in the pricking position.

A replaceable finger rest or guard 32 is detachably mounted in a slot 33 defined in the base 10A between the underside of a step 35 described below and a spaced parallel surface moulded as part of the base. The guard 32 has a hole 34 formed in its end which protrudes from the housing. The swinging arm after overrunning its neutral position will reach a limiting, operative position (shown in FIG. 5) in which it engages a step 35 in the base 10A, and the tip of the needle will then project through the hole 34 to perform a pricking operation. In that position the spring has been stretched as shown in FIG. 5 and that will return the arm to its neutral position, thus retracting the needle to a position with its tip within and guarded by the guard 32.

The finger guard 32 may be an inexpensive moulding of polyethylene or other flexible plastics material.

Figure 2:
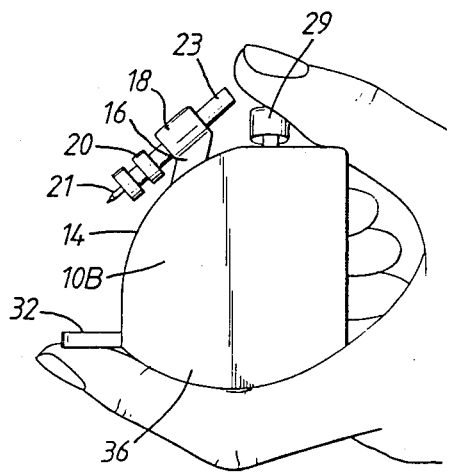
FIG. 2 is an elevation of the device of FIG. 1, ready to be used.
Figure 3:
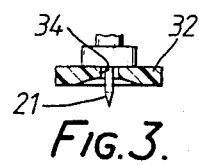
FIG. 3 is a detail showing the relationship of the needle and the finger guard when a prick is made.

Thus to operate the pricker device, the user will fit a new sterile lancet or needle 21 in the holder 18 with its needle point directed towards the guard ring, and its protuberance 23 extending out of the holder 18A, and will fit a new sterile finger and guard rest in the slot 33 having first disposed of the old needle and finger guard. He will then set the device by turning the arm back into its retracted position where it will be held by engagement with the latch 28. He will then, holding the set device in one hand as shown in FIG. 2, place the finger guard ring 32 over the pulp of a finger from which he wishes to draw a blood sample, resting that finger on the curved bottom 36 of the housing, and will then press the trigger 20 to release the latch. The arm 16 and needle 21 will fly forward under the force of the spring 25, turning about the pivot 17, and travelling through the neutral position until the arm is checked by the step at the end of the slot 15 at which time the tip of the needle is projected through the centre of the finger guard 32 to prick the patient's skin below. The arm will rebound from its limiting operative position back into its neutral position, aided by the return force of the over-centre spring 25, retracting the tip of the needle from the patient's skin to a position within the guard 32. The used needle 21 and finger guard 32 are now removed and thrown away, and a sterile replacement needle 21 and finger guard 32 fitted into the holder 18 and slot 33 for the next operation.

The used needle can be removed from the holder 18 by means of the protuberance 23. The needle can thus be displaced into a disposal receptacle without needing to be touched, so that transfer of the previous user's possibly-contaminated blood to the next user or medical personnel is avoided.

The used finger guard is also liable to carry some of the previous user's blood. The present invention enables it to be displaced into a disposal receptacle without its needing to be touched.

That is made possible by a captive bolt 66 housed in a recess formed in the base 10A.

The bottom surface 36 of the base 10A has a slot 100 formed in it affording a flat base 101 parallel to the walls of the slot 33. The captive bolt 66 has a displacing member 67 which at all times rests in the slot 33.

The bolt 66 has a ribbed activating button 68 protruding below the curve of the edge 36 of the device. The button has a flat upper face which rests on and slides over the flat base 101 of the slot 100. The slot 100 extends through the bottom wall of the housing affording an opening into its interior which opening has front and rear ends 103 and 104 which engage front and rear faces 107 and 108 of a vertical arm of the bolt 66 so as to limit its movement. The bolt 66 also carries projecting rearwardly and slightly upwardly from its rear face a retaining and screening limb 112. This interferes with access to the interior of the housing when the captive bolt is in its forward or active position (shown in FIG. 4). The limb 112 holds the captive bolt securely within the housing by bearing against the inside of the housing wall when the bolt is in its retracted or passive position (shown in FIG. 5).

The vertical arm 110 is the full width of the bolt as are the activating surface 68 and the limb 112.

The dimensions of the stem 37 of the finger guard 32, the slot 33 and the actuating member 67 are such that full forward movement of the bolt 66 (FIG. 4) fully displaces the finger guard 32 from the slot 33. The bolt is retracted (FIG. 5) ready for insertion of a new finger guard in the slot 33. However the benefits of removal of the finger guard without the need to touch it can still be achieved when the dimensions are only such that the finger guard is partly displaced so long as it will then readily fall from the slot when the device is held with the slot 33 pointing downwards e.g. vertically downwards.

We claim:

1. An automatic lancet device comprising a lancet, a mounting member and a housing with a first slot in one side through which the mounting member can move to carry the lancet over a path from a retracted to an operative position, and a finger guard positioned in the path followed by the lancet and being in juxtaposition with the lancet as the lancet makes a finger piercing movement in use; the finger guard being provided with a stem dimensioned to be removably located in a recess in the housing, said recess being spaced from said first slot, the finger guard thereby being capable of being mounted in the housing so as to be displaceable therefrom; displacement means permanently mounted on the device and movable from a first position to a second position to cause displacement of the finger guard from the slot, wherein the displacement means is a captive bolt having a limb thereon which engages the housing to hold the bolt in a second slot in the housing of the device, which second slot communicates with the recess in which the finger guard is mounted; the displacement means including an actuating member which on movement of the displacement means from the first to the second position displaces the finger guard; the displacement means further having a remote activator extending out through a surface of the housing remote from the finger guard so that a finger engaging the remote actuator can be used to move the displacement means from the first to the second position without the finger coming into contact with the finger guard.

* * * * *